(12) United States Patent
Rui

(10) Patent No.: US 12,741,115 B2
(45) Date of Patent: Sep. 22, 2026

(54) AUTOMATIC MEDICINE REPLACEMENT AND ATOMIZATION DEVICE

(71) Applicant: Medcaptain Medical Technology Co., Ltd., Shenzhen (CN)

(72) Inventor: Deng Rui, Shenzhen (CN)

(73) Assignee: Medcaptain Medical Technology Co., Ltd., Shenzhen (CN)

( * ) Notice: Subject to any disclaimer, the term of this patent is extended or adjusted under 35 U.S.C. 154(b) by 566 days.

(21) Appl. No.: 18/259,204

(22) PCT Filed: Jan. 28, 2021

(86) PCT No.: PCT/CN2021/074204

§ 371 (c)(1), (2) Date: Jun. 23, 2023

(87) PCT Pub. No.: WO2022/160197

PCT Pub. Date: Aug. 4, 2022

(65) Prior Publication Data

US 2024/0050669 A1 Feb. 15, 2024

(51) Int. Cl.
*A61M 16/14* (2006.01)
*A61M 11/00* (2006.01)
(Continued)

(52) U.S. Cl.
CPC ........ *A61M 16/14* (2013.01); *A61M 15/0003* (2014.02); *A61M 16/024* (2017.08);
(Continued)

(58) Field of Classification Search
CPC .... A61M 11/00; A61M 11/005; A61M 11/02; A61M 15/0003; A61M 15/0085;
(Continued)

(56) References Cited

U.S. PATENT DOCUMENTS 4,558,710 A * 12/1985 Eichler .................. A61B 5/411 600/533
2003/0101991 A1 * 6/2003 Trueba ............. A61M 15/0003 128/200.14

(Continued)

FOREIGN PATENT DOCUMENTS

CN 101732051 6/2010
CN 101732051 A * 6/2010

(Continued)

OTHER PUBLICATIONS

Translation of CN 101732051—Li, Guohua.

(Continued)

*Primary Examiner* — Joseph D. Boecker
(74) *Attorney, Agent, or Firm* — Jeffrey Pearce

(57) ABSTRACT

An automatic medicine exchange and atomization device includes a breathing tube, a main control module, an atomization module and a plurality of medicine solution containers. The breathing tube communicates with a patient's respiratory tract. At least one medicine solution container, each containing a corresponding medicinal liquid, communicates with the breathing tube, and is connected to the atomization module. The atomization module is electrically connected to the main control module, which controls the atomization module to atomize a solution in a selected one of the container, so that the atomized medicine solution enters the breathing tube. As the main control module controls, according to the needs of different experiments in different stages, the atomization module to atomize the medicine solution in the specific medicine solution container, thus requiring no manual replacement, and being convenient and fast.

8 Claims, 3 Drawing Sheets

(51) Int. Cl.

| | |
|---|---|
| ***A61M 11/02*** | (2006.01) |
| ***A61M 15/00*** | (2006.01) |
| ***A61M 15/02*** | (2006.01) |
| ***A61M 16/00*** | (2006.01) |
| ***A61M 16/10*** | (2006.01) |
| ***A61M 16/20*** | (2006.01) |

(52) U.S. Cl.

CPC ............ *A61M 11/00* (2013.01); *A61M 11/005* (2013.01); *A61M 11/02* (2013.01); *A61M 15/0085* (2013.01); *A61M 15/025* (2014.02); *A61M 2016/0018* (2013.01); *A61M 2016/0036* (2013.01); *A61M 16/1055* (2013.01); *A61M 16/107* (2014.02); *A61M 16/202* (2014.02); *A61M 2205/14* (2013.01); *A61M 2205/3306* (2013.01); *A61M 2205/3334* (2013.01); *A61M 2205/3386* (2013.01); *A61M 2205/3393* (2013.01); *A61M 2205/502* (2013.01); *A61M 2205/6018* (2013.01)

(58) Field of Classification Search

CPC ............ A61M 15/025; A61M 16/0051; A61M 16/01; A61M 16/024; A61M 16/04; A61M 16/0463; A61M 16/0816; A61M 16/104; A61M 16/107; A61M 16/14; A61M 16/147; A61M 16/18; A61M 16/202; A61M 2205/14; A61M 2205/3306; A61M 2205/3386; A61M 2205/3389; A61M 2205/3393; A61M 2205/6018; A61M 2016/0036

See application file for complete search history.

(56) References Cited

U.S. PATENT DOCUMENTS

| | | | | |
|---|---|---|---|---|
| 2004/0107961 | A1 | 6/2004 | Trueba | |
| 2005/0150489 | A1* | 7/2005 | Dunfield ........... | A61M 15/0083 128/200.14 |
| 2008/0011292 | A1* | 1/2008 | Sugita ................... | A61M 15/00 128/200.19 |
| 2014/0290646 | A1* | 10/2014 | Koehler ........... | A61M 16/0069 128/203.14 |
| 2017/0319797 | A1* | 11/2017 | Germinario .......... | A61M 11/003 |
| 2018/0093291 | A1 | 4/2018 | Benjamin | |
| 2021/0401038 | A1* | 12/2021 | Lawrenson ............. | A24F 40/10 |

FOREIGN PATENT DOCUMENTS

| | | | |
|---|---|---|---|
| CN | 107126607 | | 9/2017 |
| CN | 207203199 | | 4/2018 |
| CN | 109924548 | | 6/2019 |
| CN | 111653335 | | 9/2020 |
| CN | 214860116 | U | 11/2021 |
| DE | 4305277 | | 8/1994 |
| EP | 2119465 | A1 | 11/2009 |
| WO | 2020127482 | | 6/2020 |

OTHER PUBLICATIONS

Translation of CN 07126607—Taicang Hongma Software Technology Co.

Translation of CN 207203199—Suo, Chunxiu.

* cited by examiner

AUTOMATIC MEDICINE REPLACEMENT AND ATOMIZATION DEVICE

REFERENCE TO RELATED APPLICATIONS

This application is the United States national stage application under 35 U.S.C. 371 of International Application No. PCT/CN2021/074204, filed on Jan. 28, 2021, the entire contents of which are incorporated herein by reference. This is also a translation of the description and abstract of PCT/CN2021/074204; the following claims, however, differ from and supersede any amended claims under PCT Articles 19 or 34.

TECHNICAL FIELD

The present disclosure generally relates to the field of medical technologies, and more particularly, to an automatic medicine replacement and atomization device.

BACKGROUND OF THE INVENTION

A bronchial provocation test is a method to induce smooth muscle contraction in a patient's airway using physical, chemical, biological and other artificial stimulation and is the most commonly used method for measuring airway hyperresponsiveness, providing an accurate clinical examination. The change of the pulmonary function index is then used to evaluate bronchial constriction and its degree.

Stimulation of the airway by external factors can cause a spasm-contraction response; in response, the spasm-constricted airway can be relieved naturally or after treatment with bronchodilator drugs, a phenomenon called airway reversibility. Airway reactivity and airway reversibility are two important pathophysiologic al features of airway function changes. Similar to the principle of the bronchial provocation test, because it is difficult to directly measure the diameter of the airway, pulmonary function indicators are often used clinically to reflect the changes in airway function. A method of observing the soothing response of an obstructed airway by administering a bronchodilator drug is called a bronchodilator test.

The above two tests will use a variety of test liquids in clinical practice, and medical staff will frequently change different types or concentrations of liquids during each test, which is not only troublesome, but also prone to administering the wrong drug, which may lead to mistakes in the clinical treatment.

SUMMARY OF THE INVENTION

The purpose of the present application is to provide an automatic medicine replacement, that is, exchange, and atomization device, which can automatically select a specific liquid medicine for atomization without need for manual replacement and thus is convenient and quick.

To achieve the purpose of the application, the application provides the following technical solutions:

The application provides an automatic medicine exchange and atomization device. The automatic medicine exchange and atomization device includes a breathing tube, a main control module, an atomization module and a plurality of medical liquid containers. The breathing tube communicates with the respiratory tract of a patient. At least one of the medicinal liquid containers is in communication with the breathing tube. Each of the medicinal liquid containers accommodates a corresponding medicinal liquid, and a plurality of the medicinal liquid containers are connected to the atomization module, which in turn is connected to the control module. The main control module is electrically connected and is used to control the atomization module to atomize the medicinal liquid in the specific medicinal liquid container, so that the atomized medicinal liquid enters the breathing tube.

In one embodiment, the atomization module includes a switching module and an energy module, both of which are electrically connected to the main control module. The energy module inputs atomization energy to the switching module, which is used to adjust the atomization energy so that the atomization energy atomizes the specific medicinal liquid in the medicinal liquid container.

In one embodiment, the automatic medicine exchanging and atomization device further includes a one-way valve, at least one of the medicinal liquid containers is connected via a corresponding one-way valve, and the one-way valve is used to cause the liquefied medicinal liquid flow to the breathing tube.

In one embodiment, the automatic medicine exchanging and atomization device further includes a plurality of position sensors, which are used to detect the positions of the corresponding plurality of the liquid medicine containers.

In one embodiment, the one-way valve is electrically connected to the main control module, and the main control module is further configured to open the one-way valve when the patient starts aerosol therapy, and close when the patient ends the aerosol therapy.

In one embodiment, the automatic medicine exchanging and atomization device further includes a detection module electrically connected to the main control module. The detection module is used to determine the remaining amount of the medicinal liquid in the multiple medicinal liquid containers and to determine the residual amount of the medicinal liquid. A first signal is sent to the main control module, which is configured to determine whether the atomization treatment of the patient is concluded according to the first signal, so as to control the opening or closing of the one-way valve.

In one embodiment, the automatic medicine exchanging and atomization device further includes a flow sensor disposed in the breathing tube. The flow sensor is electrically connected to the switching module and is used to detect inside of the breathing tube. and send a second signal to the main control module, which is configured to control the switching module to perform atomization according to the second signal.

In an embodiment, the automatic medicine exchange and atomization device further includes a display input module, which is electrically connected with the main control module. The display input module is used to input a third input signal to the main control module, which then identifies the specific chemical liquid container, the atomization amount and the atomization times of the chemical liquid in the specific chemical liquid container according to the third signal.

In one embodiment, the automatic medicine exchanging and atomization device further includes a filter disposed in the breathing tube. The filter is used to filter the gas in the breathing tube.

In one embodiment, the automatic medicine exchange and atomization device further includes a liquid medicine detection module, and the liquid medicine detection module is used to detect the type and/or concentration of the liquid medicine in the plurality of liquid medicine containers.

By setting the electrical connection between the main control module and the atomization module, the main control module can control the atomization module to atomize the liquid medicine in a specific liquid medicine container according to the needs of different stages of the experiment, without manual replacement, which is convenient and fast.

BRIEF DESCRIPTION OF THE DRAWINGS

In order to more clearly illustrate the embodiments of the present application or the technical solutions in the prior art, the following briefly introduces the drawings that are used in the description of the embodiments or the prior art. Obviously, the drawings in the following description are only some embodiments of the present application, and for those of ordinary skill in the art, other drawings can also be obtained from these drawings without creative effort.

DETAILED DESCRIPTION

The technical solutions in the embodiments of the present application will be clearly and completely described below with reference to the drawings showing embodiments described in this application. Obviously, the described embodiments are only some of the possible embodiments, all of the embodiments. Based on the embodiments described in this disclosure, all other embodiments obtained by those of ordinary skill in the art without creative work fall within the protective scope of this application.

Figure 1:
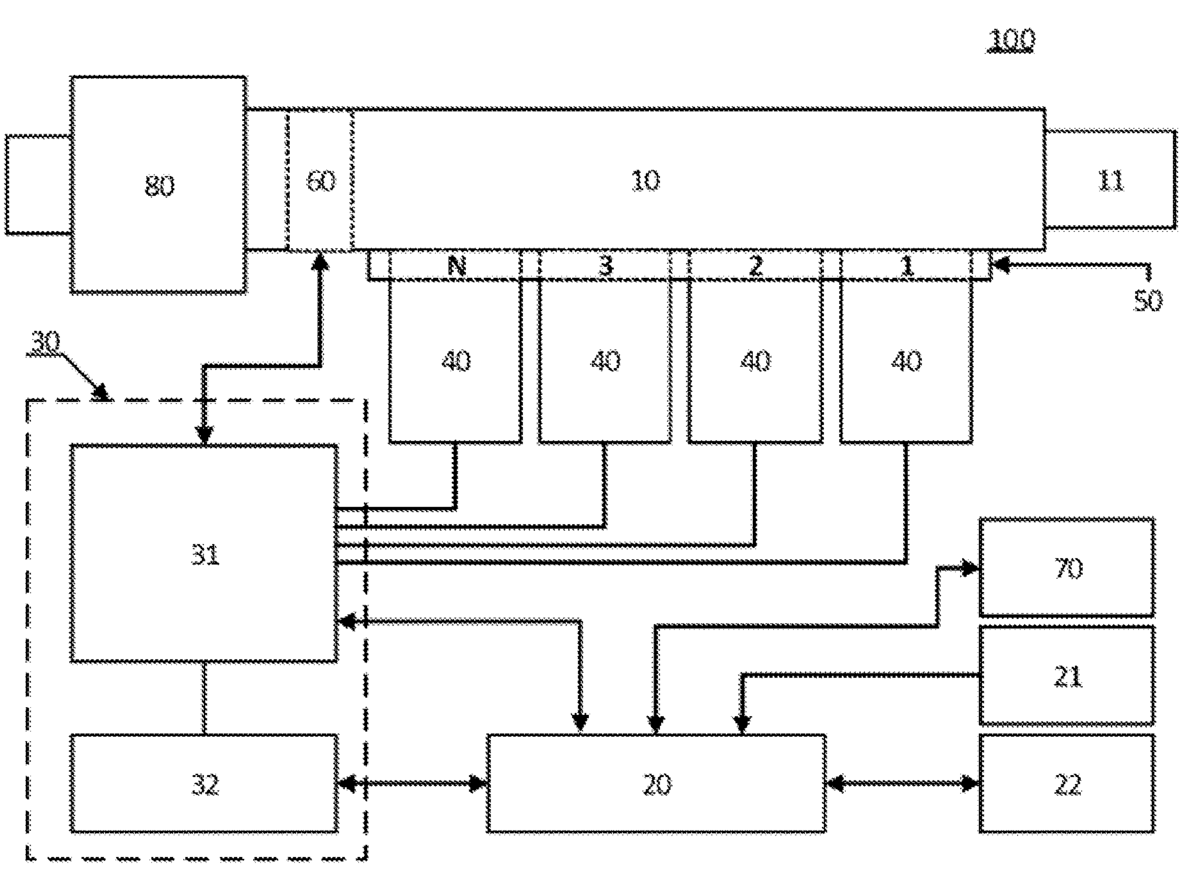
FIG. 1 is a schematic structural diagram of an automatic medicine exchanging and atomization device provided by an embodiment according to this disclosure.

Please refer to FIG. 1, which illustrates that an embodiment of provides an automatic medicine exchanging and atomization device 100. The automatic medicine exchanging and atomization device 100 is any medical device such as a pulmonary function meter, an oxygen generator, and a nebulizer, for example, a jet nebulizer, hand-pinch nebulizer, ultrasonic nebulizer, etc. The automatic medicine exchanging and atomization device 100 includes a breathing tube 10, a main control module 20, an atomization module 30 and a plurality of medical liquid containers 40. The breathing tube 10 communicates with the patient's airway. At least one medicinal liquid container 40 communicates with the breathing tube 10, and each medicinal liquid container 40 accommodates a corresponding medicinal liquid. The plurality of liquid medicine containers 40 are all connected to the atomization module 30, and the atomization module 30 is electrically connected to the main control module 20. The main control module 20 is used to control the atomization module 30 to atomize the medicinal liquid in the specific medicinal liquid container 40, so that the atomized medicinal liquid enters the breathing tube 10.

Specifically, one end of the breathing tube 10 is provided with a mouthpiece 11, and the other end communicates with the outside air or an air supply device such as a ventilator. The automatic medicine exchanging and atomization device 100 further includes an interface assembly 50, which is connected to medicinal liquid containers 40 (labeled 1, 2, 3, . . . , N) and the breathing tube 10. In this embodiment, four liquid medicine containers 40, arranged in a line, are depicted, all of which communicate with the breathing tube 10 through the interface assembly 50. In other embodiments, the interface assembly 50 can be used to switch different medicinal liquid containers 40 to communicate with the breathing tube 10, so that the medicinal liquid container 40 containing the medicinal liquid required for atomization (for example, container 1) is allowed to communicate with the breathing tube 10. The temporarily unused medicinal liquid containers 40 (for example, 2–N) remain connected to the breathing tube 10, but not in communication with, that is, open to, the breathing tube 10. In addition, the medicinal 1 container 40 can be provided with a sealing structure (not shown) at the opening, and the sealing structure can prevent the medicinal solution in the medicinal solution container(s) 40 that are not being used temporarily from evaporating to the outside world, or to prevent medicinal solution entering the breathing tube 10. The medicinal liquid in the container 40 may evaporates into the breathing tube 10 during non-atomization periods, and at the same time, the sealing structure can be actively opened under the condition of internal positive pressure or external negative pressure, so that the medicinal liquid in the proper medicinal liquid container 40 can be atomized so that it can be absorbed by the patient. The number of the liquid medicine containers 40 may be two, three, five, six, . . . and not just the four shown in the figures. The plurality of medical liquid containers 40 may be arranged in different ways, such as in a circle or square around the outer circumference of the breathing tube 10.

It can be understood that there may be differences in the concentration and type of the liquid medicine required in different tests or different stages of the same test. Existing atomization devices require manual replacement of the liquid medicine before the next atomization can be performed. However, in the automatic medicine exchanging and atomization device 100 provided by embodiments of this invention, by setting the main control module 20 and the electrically connected atomization module 30, the main control module 20 can control the atomization module 30 to atomize a specific medicine according to the needs of different stages of the experiment. The medicinal liquid in the liquid container 40 does not need to be manually replaced, which is convenient and quick.

Figure 2:
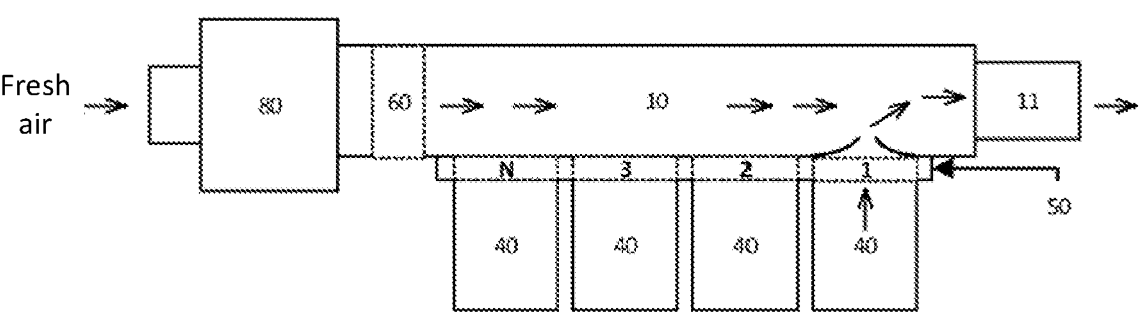
FIG. 2 is a partial structure schematic diagram of the automatic medicine replacement and atomization device when the patient inhales.

In one embodiment, illustrated in FIG. 1, the atomization module 30 includes a switching module 31 and an energy module 32. Both the switching module 31 and the energy module 32 are electrically connected to the main control module 20. The energy module 32 inputs the atomization energy to the switching module 31, and the switching module 31 is used to allocate the atomization energy, so that the atomization energy atomizes the liquid medicine in the specific liquid medicine container 40. Specifically, the atomization energy may be energy that can atomize the medicinal liquid, such as compressed gas or ultrasonic energy. The switching module 31 has a plurality of channels, each channel communicating with a respective one of the liquid medicine containers 40. The switching module 31 can allocate the atomization energy so that the atomization energy is distributed to the specific liquid medicine container 40 in a specific ratio. For example, The switching module 31 may distribute the atomization energy to the No. 1 medicinal solution container 40, No. 2 medicinal solution container 40 and No. 3 medicinal solution container 40 in a ratio of 1:4:3, so that the combined medicinal solution is atomized into the breathing tube 10 according to the specific ratio. Of course, as FIG. 2 depicts, when only a single medicinal liquid is required, the switching module 31 can also provide all the atomization energy provided by the energy module 32 to the medicinal liquid container 40 (such as No. 1) with the selected medicinal liquid.

Figure 3:
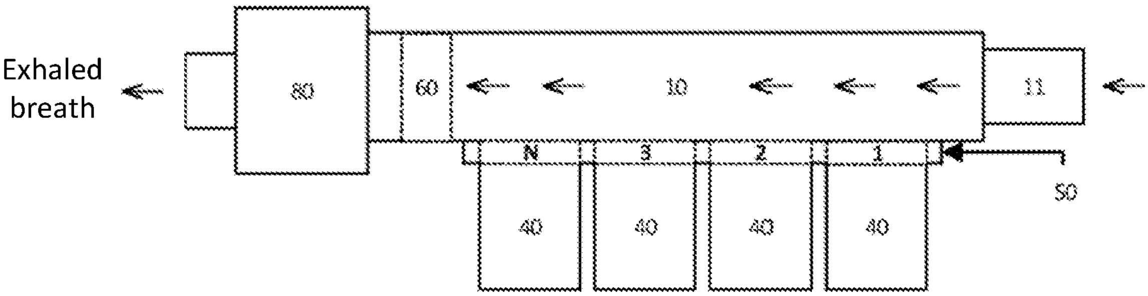
FIG. 3 is a partial structural schematic diagram of the automatic medicine replacement and atomization device when the patient exhales.
Figure 4:
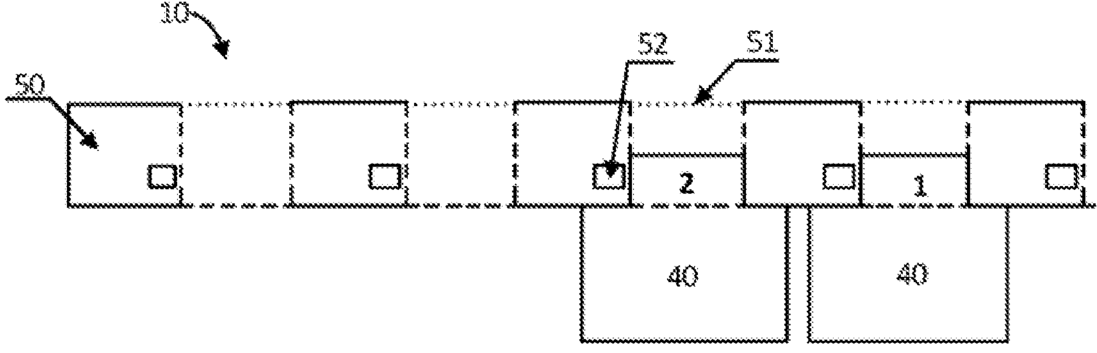
FIG. 4 is a structural representation of an interface assembly and the medicinal liquid container of FIG. 1.

In one embodiment, illustrated in FIG. 3 and FIG. 4, the automatic medicine exchanging and atomization device 100 further includes at least one one-way valve 51. At least one of the medicinal liquid containers 40 is connected with the corresponding one-way valve 51, which is used to make the medicinal liquid move toward the breathing tube 10 in one direction. Specifically, in this embodiment, the number of one-way valves 51 is the same as the number of the liquid medicine containers 40, each of which is connected with a corresponding one-way valve 51. In other embodiments, the number of the one-way valves 51 may be less than the number of the medical solution containers 40, with only some of the medical solution containers 40 (one or more) being connected with the one-way valves 51. The one-way valve 51 is arranged at the interface between the breathing tube 10 and the liquid medicine container 40. The aerosolized liquid medicine can only reach the breathing tube 10 from the liquid medicine container 40 through the one-way valve 51, but cannot pass backward from the breathing tube 10 to the liquid medicine container 40. The atomized medicinal liquid can then be fully contained in the breathing tube 10 and absorbed by the patient. In addition, the one-way valve 51 can ensure that the gas and liquid in the breathing tube 10 will not enter the medicinal liquid container 40, so as to avoid the medicinal liquid in the medicinal liquid container 40 from being contaminated.

In one embodiment, illustrated in FIG. 4, the automatic medicine exchanging and atomization device 100 further includes a plurality of position sensors 52. The plurality of position sensors 52 are used to detect the positions of the corresponding plurality of chemical solution containers 40. Specifically, the position sensor 52 may detect the position of the liquid medicine container 40 by methods such as photoelectric detection and magnetic detection. The number of the position sensors 52 and the liquid medicine containers 40 is the same and in one-to-one correspondence. Each position sensor 52 senses whether the corresponding liquid medicine container 40 is in place. The position sensor 52 is electrically connected to the main control module 20, so as to send the position information of the medicinal liquid container 40 to the main control module 20.

It can be understood that, before starting the atomization function, it is necessary to ensure that the liquid medicine container 40 with the liquid medicine required for the test is properly in the corresponding position. For example, illustrated in FIG. 4, this test needs to use the medicinal liquid in the No. 1 chemical liquid container 40 and the chemical liquid in the No. 2 chemical liquid container 40. The No. 1 chemical liquid container 40 and the No. 2 chemical liquid container 40 are located at the two ports on the right side, so before starting the test, the atomization function needs to be confirmed by the two position detectors corresponding to the container number. Of course, the position sensor 52 can also be used to detect whether there is a liquid medicine container 40 in the corresponding interface, and send the information about the presence of the liquid medicine container 40 to the main control module 20, and then determine the required medicine after determining the type of the test.

By arranging a plurality of position sensors 52, the plurality of position sensors 52 can determine the position information of the liquid medicine container 40 at the corresponding position, so that the liquid can be added manually or by other modules, or the required medicine can be added in the corresponding position.

In one embodiment, the one-way valve 51 is electrically connected to the main control module 20. The main control module 20 is also used to open the one-way valve 51 when the patient starts the aerosol therapy, and close the one-way valve 51 when the patient completes the aerosol therapy. Specifically, the plurality of one-way valves 51 are all electrically connected to the main control module 20. The main control module 20 can open the one-way valve 51 during the entire breathing process of the patient's aerosol therapy, or open the one-way valve 51 during the inhalation process of the patient's aerosol therapy, and close the one-way valve 51 during the exhalation phase of the breathing process. It can be understood that when the one-way valve 51 is opened, any solvent included in the medicinal solution in the corresponding medicinal solution container 40 will easily evaporated which will cause the concentration of the medicinal solution to increase, which will in turn cause the amount of medicinal solution inhaled by the patient in the next atomization treatment to exceed the standard. When the patient does not need aerosol treatment, closing the one-way valve 51 can ensure that the concentration of the medicinal solution in the medicinal solution container 40 in place does not change.

In one embodiment, the automatic medicine exchange and atomization device 100 further includes a detection module (not shown) electrically connected to the main control module 20. The detection module is used to determine the remaining amount of the medicinal solution in the multiple medicinal solution containers 40 and send the first signal to the main control module 20. The main control module 20 is used for judging whether the atomization treatment of the patient is finished according to the first signal, so as to control the one-way valve 51 to open or close. By setting the detection module, the detection module can determine the remaining amount in the liquid medicine container 40 and send the first signal to the main control module 20, so that the main control module 20 can judge whether the atomization treatment is over, which is beneficial to the intelligent use of the automatic medicine exchange and atomization device 100

In this embodiment, the detection module can confirm the remaining amount of the liquid medicine in the liquid medicine container 40 by weighing or other means, and send the first signal to the main control module 20, which then controls the atomization module 30 according to the first signal.

In other embodiments, the main control module 20 can deduce the amount of liquid medicine that can be atomized per unit of atomization energy according to the atomization energy and atomization amount in multiple atomization processes. In the subsequent atomization process, it may calculate the remaining amount of the liquid medicine according to the atomization time. In addition, by controlling the atomization time, quantitative atomization can be achieved.

In one embodiment, as illustrated in FIG. 1, the automatic medicine exchanging and atomization device 100 further includes a flow sensor 60 disposed in the breathing tube 10. The flow sensor 60 is electrically connected to the switching module 31. The flow sensor 60 is used to detect the flow in the breathing tube 10 and send a second signal to the main control module 20. The main control module 20 then controls the switching module 31 to perform atomization according to the second signal. Specifically, the flow sensor 60 may be a thermal sensor, a differential pressure sensor, an ultrasonic sensor, or other sensors capable of measuring flow. By including the flow sensor 60, the flow sensor 60 may detect the flow in the breathing tube 10 in real time, thereby monitoring the breathing waveform of the patient, so that the main control module 20 can perform aerosol administration at the appropriate position of the patient's pulmonary cycle, which is beneficial to improve the efficiency of aerosol absorption and improves both efficiency and comfort to the patient being nebulized. It can be understood that the main control module 20 can determine the inspiratory phase and the expiratory phase during the patient's breathing process through the second signal sent by the flow sensor 60, and calculate the phase at which atomization should start in the inspiratory phase according to the amount of atomization and atomization time. Typically, the phase at which nebulization begins is somewhere between the beginning of inspiration and the end of inspiration.

In one embodiment, illustrated in FIG. 1, the atomization device 100 for automatic medicine exchange further includes a display input module 70, which is electrically connected to the main control module 20. The display input module 70 is used for inputting a third signal to the main control module 20, which then determines the specific liquid medicine container 40, the atomization amount and the number of atomization times of the liquid medicine in the specific liquid medicine container 40 according to the third signal. Specifically, the display input module 70 can display state parameters such as the type of liquid medicine being atomized and administered to the patient, the remaining amount of the liquid medicine, the atomization time and the number of atomizations, and the medical staff can obtain the patient's atomization treatment progress through the display input module 70. At the same time, the medical staff can customize the atomization volume of the patient, the number of times of atomization and the atomization time of the specific liquid medicine through the display input module 70, so as to adjust the test parameters according to the actual situation of the patient.

In this embodiment, the main control module 20 is further provided with a power supply interface 21 and a communication interface 22. The power supply interface 21 is used for electrical connection with an external power supply (not shown) so as to supply power to the main control module 20 and other modules. The communication interface 22 is used to communicate with electronic devices such as computers, smart phones, and remote controls, so as to facilitate remote control and centralized control, and is conducive to reducing manpower requirements.

In one embodiment, illustrated in FIG. 1, the automatic medicine exchanging and atomization device 100 further includes a filter 80 disposed on the breathing tube 10. The filter 80 is used to filter the gas in the breathing tube 10. It can be understood that the filter 80 of the breathing tube 10 can effectively prevent cross infection of the patient's saliva or exhaled exhaust gas, which is beneficial to avoid the deterioration of the patient's condition.

In one embodiment, the atomization device 100 for automatic medicine exchange further includes a medicinal liquid detection module (not shown). The medicinal liquid detection module is used to detect the types and/or concentrations of medicinal liquids in the plurality of medicinal liquid containers 40. Specifically, the medicinal liquid detection module is electrically connected to the main control module 20. After the liquid medicine detection module detects the types and/or concentrations of the medicinal liquids in the plurality of liquid medicine containers 40, a fourth signal is sent to the main control module 20. Cooperating with the medicinal liquid detection module and the position sensors 52, the main control module 20 can determine the type and/or concentration of the medical liquid container 40 in place and the solution in it, the main control module 20 can control the specific type and concentration of the medical solution required by the patient to be nebulized, and open its corresponding one-way valve 51, so as to realize automatic drug administration to the patient. In addition, the automatic medicine exchanging and atomization device 100 can also be provided with a medicine-adding module (not shown), which is electrically connected to the main control module 20. When the detection module detects that the amount of liquid medicine is insufficient, the main control module 20 can control the medicine adding module to replenish the medicine solution to the medicine solution container 40 with insufficient medicine solution. When the liquid medicine detection module finds that the concentration of the liquid medicine is too high or too low, the main control module 20 can control a dosing module to add solvent or solute to its liquid medicine container 40 to adjust the concentration of the liquid medicine to a desired level.

Figure 5:
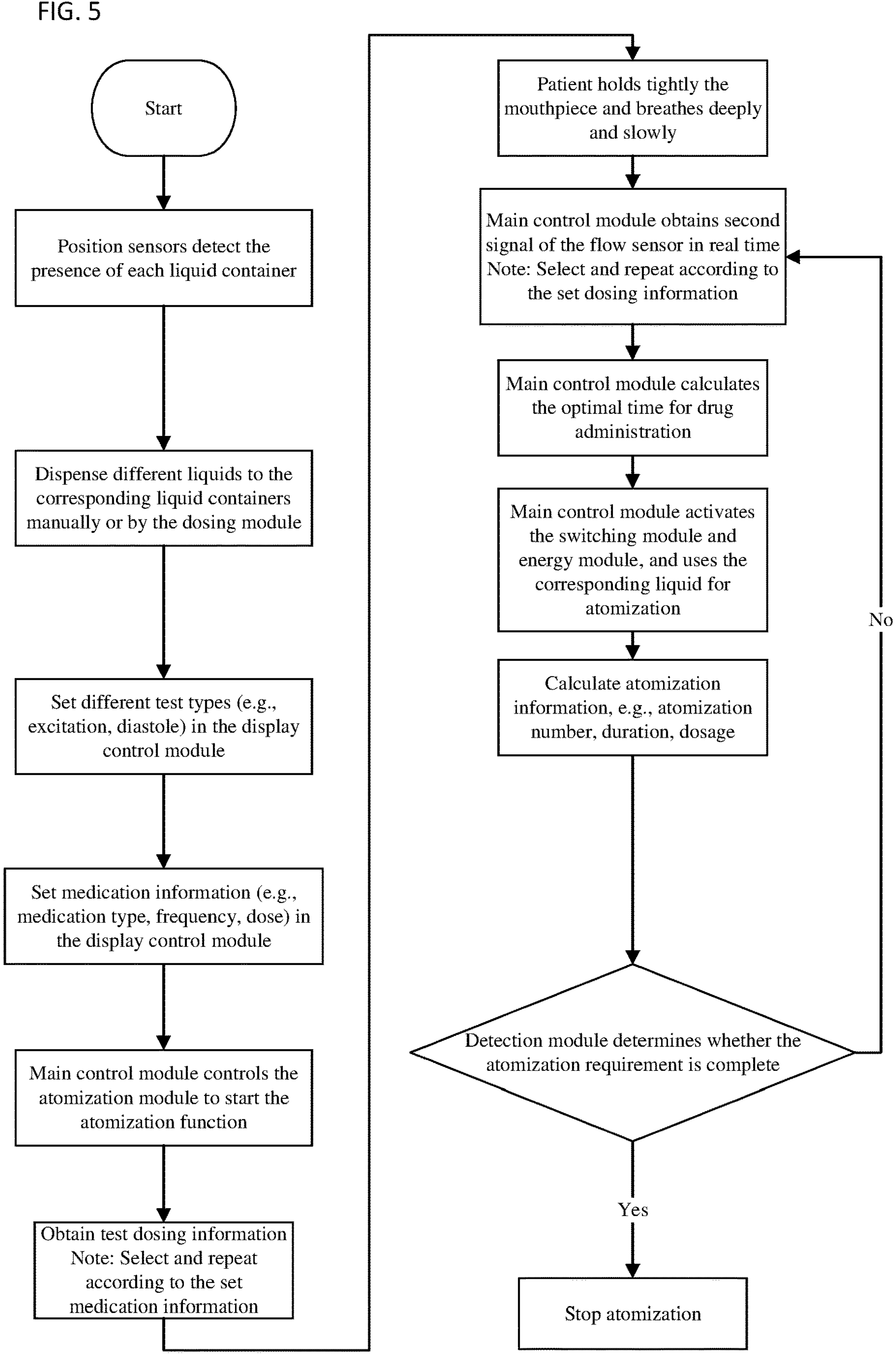
FIG. 5 is a working flow chart of an automatic medicine replacement and atomization device according to an embodiment.

Refer to FIG. 1 and FIG. 5—in which the illustrated embodiment further provides an atomization workflow of the atomization device 100 for automatic medicine exchange.

S1: The medical staff first place the configured medicinal solution on the medicinal solution container 40 at the corresponding numbered position of the interface assembly 50, for example, place the three medicinal solutions A, B, and C at the positions corresponding to the interfaces 1, 2, and 3, respectively;

S2: The position sensor 52 of the interface assembly 50 can identify the insertion of the medicinal solution container 40 in real time, and the operator can see the presence information on the display input module 70, and distribute the corresponding medicinal solution to the medicinal solution container 40 at the designated position;

S3: Medical staff set different test types, such as provocation test or relaxation test, etc.;

S4: According to the set test type, customize the medication information, such as the medication type, frequency, dose, etc. (medication information can be input in the display input module);

S5: the main control module 20 controls the atomization module 30 to start the atomization function;

S6: the main control module 20 obtains medication setting information (the medication setting information can be displayed by the display input module);

S7: The medical staff instructs the patient to hold the mouthpiece 11 and breathe deeply and slowly;

S8: the main control module 20 acquires the second signal of the flow sensor 80 in real time, and calculates the optimal medication position in real time;

S9: The main control module 20 activates the energy module 32 and the switching module 31 according to the optimal medication position, and selects to use the corresponding medicinal solution to activate the atomization function. As shown in FIG. 2, the No. 1 medicine is selected during the aerosol inhalation. The medicine in the liquid container 40, driven by the energy module 32, that is, the medicinal liquid in the No. 1 medicinal liquid container 40, starts to be atomized, and the main control module 20 controls the one-way valve 51 to open, and the atomized medicinal liquid is sent to the breathing tube 10. The patient inhales the medicine into the body due to the negative pressure in the body when inhaling;

S10: The detection module calculates the current medication information in real time, such as statistics of the current medication information and calculation of the remaining medication amount. As shown in FIG. 3, after the second atomization medication is completed, the main control module 20 will turn off the switching module 31 and the energy module 32, which causes the one-way valve 51 corresponding to the No. 1 drug solution container 40 to be closed. The atomization function is thereby turned off, and when the subject exhales, the air flow is discharged from the other end of the breathing tube 10.

S11: The detection module determines whether the atomization is completed, and if it is completed, the atomization function is stopped; otherwise, the operation is repeated from S8 until the medication is completed.

The detection module may be a sub-module of the switching module 31 or the energy module 32, that is, the detection module is integrated with the switching module 31 or the energy module 32.

The above disclosure is only a preferred embodiment of the present application, and of course, it cannot limit the scope of rights of the present application. Those of ordinary skill in the art can understand that all or part of the process of implementing the above-mentioned embodiment can be realized according to the right of the present application. The equivalent changes required are still within the scope of the application.

What is claimed is:

1. An automatic medicine exchange and atomization device for nebulization of a patient, comprising:

a breathing tube;

a main control module;

an atomization module that is electrically connected with the main control module;

a plurality of containers of respective medicinal liquids connected to the atomization module;

at least one one-way valve, in which:

at least one of the containers is connected with a corresponding one of the one-way valves;

the breathing tube is configured to be in fluid communication with a patient's respiratory tract;

at least one of the plurality of containers is in fluid communication with the breathing tube;

the main control module is provided to cause the atomization module to selectively atomize at least one of the medicinal liquids in the corresponding containers, whereby each atomized selected medicinal liquid enters the breathing tube; and said one-way valve is provided for restricting flow of the selected medicinal liquid to only an inhalation direction within the breathing tube.

2. The automatic medicine exchange and atomization device of claim 1, further comprising:

a switching module and an energy module, both of which are included in the atomization module and are electrically connected to the main control module;

in which:

the energy module is provided for inputting atomization energy to the switching module, said atomization energy causing the atomization of the at least one selected liquid medicine in the respective container.

3. The automatic medicine exchange and atomization device as in claim 2, further comprising:

a flow sensor arranged in the breathing tube, the flow sensor being electrically connected with the switching module and being configured to detect flow in the breathing tube and generating a second signal corresponding to the detected flow;

in which the main control module is configured to control the switching module to perform atomization according to the second signal.

4. The automatic medicine exchange and atomization device as claimed in claim 1, further comprising a plurality of position sensors, each detecting positions of the corresponding plurality of containers within the device.

5. The automatic medicine exchange and atomization device of claim 1, in which each one-way valve is electrically connected to the main control module, said main control module being further configured to open the respective one-way valve when the patient starts nebulization, and close the one-way valve when the patient completes nebulization.

6. The automatic medicine exchange and atomization device of claim 1, further comprising:

a detection module electrically connected to the main control module, said detection module determining a remaining amount of the medicinal liquid in at least one of the plurality of containers and sending a corresponding first signal to the main control module, said main control module being further configured to determine conclusion of nebulization of the patient according to the first signal, so as to control the one-way valve to open or close.

7. The automatic medicine exchange and atomization device as in claim 1, further comprising:

a display input module electrically connected with the main control module and generating and communicating to the main control module a third signal;

in which:

the main control module is configured to determine an atomization amount and a number of times of atomization of the selected one of the medicinal liquids according to the third signal.

8. The automatic medicine exchange and atomization device as in claim 1, further including a filter arranged in the breathing tube, said filter filtering gas within in the breathing tube.

* * * * *